United States Patent [19]

Shillington et al.

[11] Patent Number: 4,702,385
[45] Date of Patent: Oct. 27, 1987

[54] HOSPITAL IN-ROOM DISPOSABLE CONTAINER

[75] Inventors: Richard A. Shillington, San Clemente; Alec Oberschmidt, Leucadia, both of Calif.

[73] Assignee: Med-Safe Systems, Inc., Encinitas, Calif.

[21] Appl. No.: 30,353

[22] Filed: Mar. 26, 1987

[51] Int. Cl.⁴ ............................................. B65D 25/24
[52] U.S. Cl. ..................................... 220/18; 220/1 T; 220/408; 220/210
[58] Field of Search .................. 220/1 T, 18, 210, 229, 220/401, 404, 408

[56] References Cited

U.S. PATENT DOCUMENTS

| | | | |
|---|---|---|---|
| 3,057,506 | 10/1962 | Wetlesen | 220/18 |
| 4,487,331 | 12/1984 | Hawker | 220/1 T |
| 4,502,606 | 3/1985 | Shillington et al. | 220/229 |

Primary Examiner—George T. Hall
Attorney, Agent, or Firm—Baker, Maxham & Jester

[57] ABSTRACT

A disposable container assembly comprises an open top housing for receiving an inner disposable container having a lockable cap and a bracket assembly for permanent attachement to a stationary object and lock latching means for securing the outer container to the bracket and for lockably securing the inner container in a position inside the outer container.

16 Claims, 4 Drawing Figures

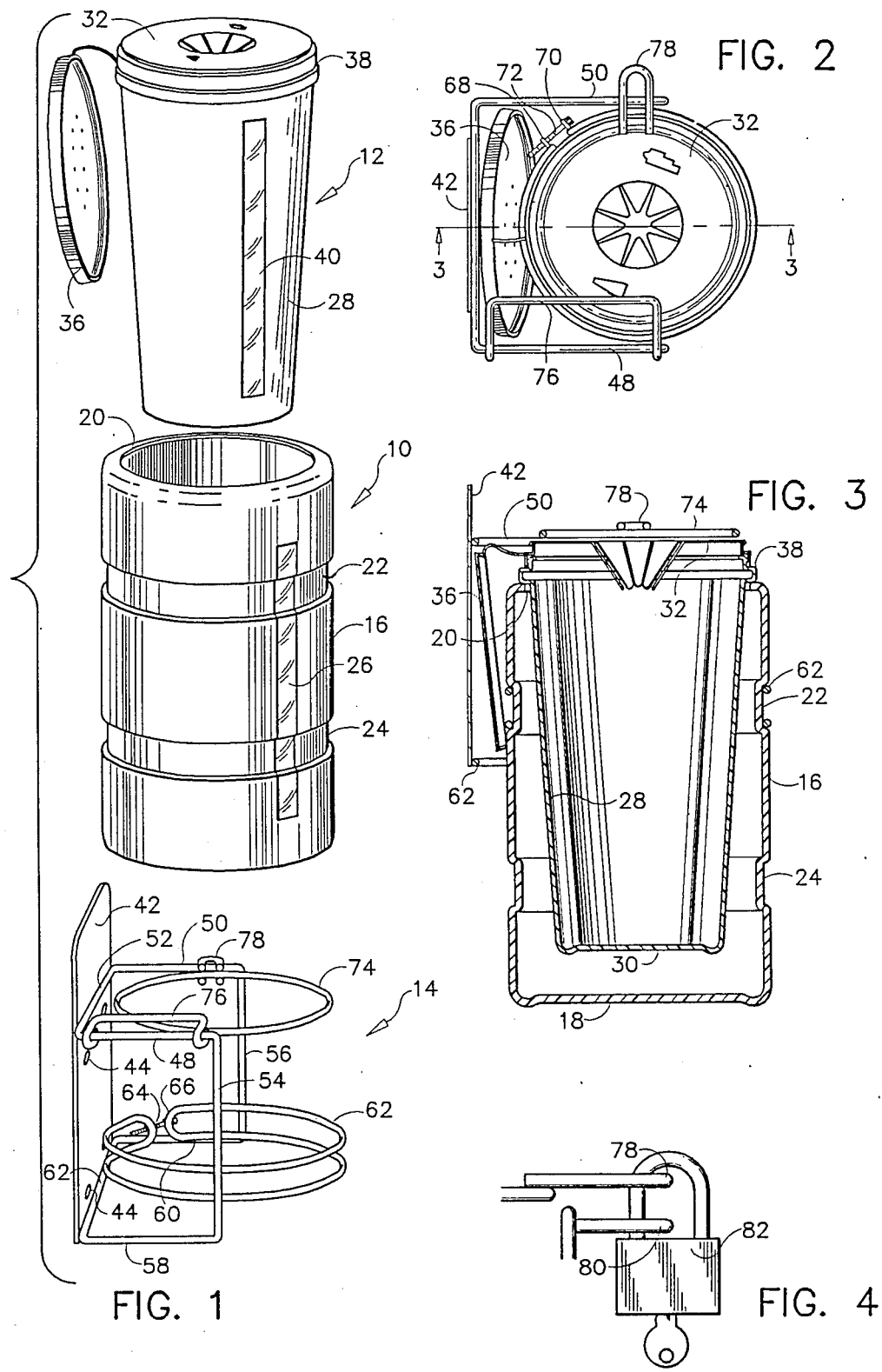

HOSPITAL IN-ROOM DISPOSABLE CONTAINER

BACKGROUND OF THE INVENTION

The present invention relates to disposable containers and pertains particularly to a securable disposable container for containment and disposition of hospital sharps, objects and waste.

Disposable containers have been developed in recent years which provide a reasonably high degree of security for disposable articles and materials from hospitals and clinics. Many of these articles, known as sharps, and other similar articles and materials must be disposed of in a manner to keep them out of the hands of unauthorized persons and to keep them from being reused. These containers are designed to prevent the removal of materials from the container under ordinary circumstances. However, these containers must normally be kept in a secure place and carried around from place to place in a hospital or clinic as needed. One such container of the aforementioned type is that of our prior U.S. Pat. No. 4,502,606, issued Mar. 5, 1985, and directed to a locking closure for disposable containers. These containers, however, can be removed from their location unless special provisions are made for securing them in place.

There is a lack of suitable containers for placement in hospital rooms and the like such that they have a reasonable means of security.

It is, therefore, desirable that a disposable container is available which may be securely placed in various locations throughout hospitals, clinics and the like, and retain the security while retaining ease of use and disposition.

SUMMARY AND OBJECTS OF THE INVENTION

It is, therefore, the primary object of the present invention to provide an improved secure disposable container assembly.

In accordance with the primary aspect of the present invention, a disposable container comprises an outer rigid container and an inner rigid securable disposable container with bracket means for securing to a fixed structure and for securing the inner container in the outer container.

BRIEF DESCRIPTION OF THE DRAWING

The above and other objects and advantages of the present invention will become apparent from the following description when read in conjunction with the drawings wherein:

FIG. 1 is an exploded perspective view of the invention;

FIG. 2 is a side elevation view partially in section of the container assembly of FIG. 1;

FIG. 3 is a top view of the container assembly of FIG. 1; and,

FIG. 4 is an enlarged detailed view taken on line 4—4 of FIG. 1.

DETAILED DESCRIPTION OF A PREFERRED EMBODIMENT

Referring to FIG. 1 of the drawings, a disposable container assembly, in accordance with the invention, comprises an outer container or housing designated generally by the numeral 10, a disposable inner receptacle or container designated generally by the numeral 12, and an anchoring and retainer bracket designated generally by the numeral 14. The housing 10 comprises a generally cylindrical container having or defined by vertical generally cylindrical walls 16, a bottom 18 and an open top or top opening defined by the upward terminus of the walls and inwardly directed peripheral flanges 20. The outer wall of the container is provided with one or more circular or peripheral recesses 22 and 24, as illustrated, for receiving and cooperating with clamps or brackets for securing it in place.

The outer container is preferably made of a rigid plastic material, such as polypropylene or the like, and preferably includes an elongated window 26 extending vertically along at least one side of the container. This window enables viewing the contents of the interior of the container to determine the extent to which it is filled.

The inner disposable container comprises frusto conical shaped walls 28 integral with and extending upward from a flat circular bottom 30, and terminating in an upper end or top formed of a circular or peripheral rim defining a circular opening. The opening is surrounded with suitable peripheral retaining means for retainign a one-way closure cap 32 having a funnel shaped one-way pass-through closure opening 34 and a permanent closure cover 36. These closure assemblies are disclosed in detail in our prior U.S. Pat. No. 4,502,606 described above and incorporated herein by reference as though fully set forth.

The disposable inner container 12 includes a radial peripheral rim 38 for overlying the rim 20 for securing peripheral in position, as will be explained. The disposable containers are designed to nestle such that a great number of the containers may be nestled together and shipped in small containers. This enables the disposable container to be shipped and stored in quantities in small space.

The disposable inner container 12 is designed and preferably constructed of a material that is at least as tough and durable as that of the housing or outer container 10 and for disposal. The material is preferably polypropylene and may be rigid or semi-rigid but is thicker and tough at the corners to resist puncture by needles and the like. It may also be transparent or provided with a window 40 aligned with window 26 of the housing so that the contents therein may be viewed to determine if the container has been filled or not. Alternatively, the top 32 of the disposable inner container may be transparent for viewing the contents thereof to ascertain the level of the contents.

A retainer clamp and bracket assembly, as illustrated, comprises a back plate 42 of a generally square or rectangular configuration, preferably constructed of stainless steel or the like. The base or back plate is stainless steel or the like. The base or back plate is securement to a permanent stationary structure, such as a bed frame or the like. The bracket further comprises an outwardly extending support arm assembly formed of a continuous looped endless wire or rod formed into a pair continuous looped endless wire or rod formed into a pair comprises a pair of upper outwardly extending arm members 48 and 50 connected together by an inner horizontal member 52 secured such as by welding to the face of plate 42. The arm members 48 and 50 are connected by vertical members 54 and 56 to lower outwardly extending arm members 58 and 60, which are connected together at their inner ends by a horizontal member 62.

The horizontal member 62 is secured as by welding to the face of plate 42.

The bracket assembly 14 further comprises a generally circular clamp member 46, preferably constructed like a hose clamp of a continuous loop of wire or rods extending around in a circle with adjacent free ends 64 and 66. The free ends 64 and 66 are provided with a pair of lock receiving brackets or holes 68 and 70 for receiving a bolt or screw 72 for drawing the ends together for encircling and clamping into the recess 22 of the housing.

The pair of lock or screw receiving eyes or brackets 68 and 70 are formed or mounted at the ends of the clamp 62 for receiving a screw and nut or a lock as may be required. A lock may also take the form of a special screw which requires a special instrument for removal. For example, instead of a screw slot for a bladed or Philips screwdriver, the head of the screw may contain a socket of an unusual shape requiring a special tool available only to one or more staff members of a hospital or clinic. Thus, the bracket has the normal security of a locked bracket.

A lockable retaining latch or clamp at the upper end of the bracket is designed to engage and retain the disposable inner container within the inside of the outer container. This bracket assembly comprises a rod or wire ring or circular member 74 pivotaly mounted or hinged to the outward extending arm 48 by a hinge member 76. A lock receiving eye or loop 78 is secured to the ring 74 on the opposite side from the hinge 76. This lock eye cooperates with a fixed eye or loop 80 secured to the opposite horizontal arm 50. A conventional padlock 82 having tines 84 extending through the eyes 78 and 80 for locking the clamp ring 74 against the top 32 of the disposable container 12. Thus, a disposable inner container 12 may be lockably secured inside an outer container or housing 10.

In operation, a bracket 14 as above described is selected and mounted in a hospital room, clinic room or the like to a secure structure, such as a bed frame or the like. A housing 10 is then mounted in the bracket by extending clamp 62 around the container within the groove 22, and securing it in place by means of a suitable bolt or the like extending through the eyes or brackets 68 and 70, as shown in FIG. 3. With the outer container in place, the upper clamp 74 is swung back to provide access to the open top of the housing 10. A disposable container is then selected and inserted in the open top of the housing 10 and seated with the radial rim 38 thereof resting on or engaging the rim 20 of the housing 10. The clamp member 74 is then hinged or swung over into clamping position, and a lock 82 is inserted through the brackets 78 and 80 securing the disposable inner container in place in the housing. This then provides an assembly wherein a disposable container is securely locked within a permanently mounted housing. The disposable container may be readily removed for disposal when filled. The windows 26 and 40 in the outer and inner containers, respectively, permit viewing the contents of the container to establish the degree of filling thereof and ascertain when replacement is required.

While we have illustrated and described our invention by means of specific embodiments, it is to be understood that numerous changes and modifications may be made therein without departing from the spirit and scope of the invention as defined in the appended claims.

We claim:
1. A disposable container assembly comprising:
 a housing having a top and an opening in said top for receiving a disposable container;
 a disposable container removably disposed in said opening within said housing; and
 latch lock frame means for locking said disposable container in place in said housing.
2. A disposable container assembly according to claim 1 wherein:
 said latch lock means comprises a base for attachment to support structure, first arm means for detachably securing said housing to said support structure, and second arm means for lockably securing said disposable container in said housing.
3. A disposable container assembly according to claim 1 wherein:
 said housing is cylindrical in configuration and said opening is circular.
4. A disposable container assembly according to claim 1 wherein:
 said disposable container has a circular opening for positioning within said housing opening and has a one-way pass-through closure disposed therein and a locking closure therefor.
5. A disposable container assembly according to claim 1 wherein:
 said housing has transparent window means therein for viewing the contents of said disposable container.
6. A disposable container assembly according to claim 1 wherein:
 said housing is defined by upstanding cylindrical walls terminating in a circular rim defining said opening; and
 said disposable container is defined by generally frusto conical walls terminating in circular rim defining an opening and a radial flange for engaging said circular rim.
7. A disposable container assembly according to claim 6 wherein:
 said disposable container has a circular opening for positioning within said housing opening and has a one-way pass-through closure disposed therein and a locking closure therefor.
8. A disposable container assembly according to claim 7 wherein:
 said housing has transparent window means therein for viewing the contents of said disposable container.
9. A disposable container assembly according to claim 8 wherein:
 said housing is defined by upstanding cylindrical walls terminating in a circular rim defining said opening; and
 said disposable container is defined by generally frusto conical walls terminating in circular opening and a radial flange surrounding said opening for engaging said circular rim.
10. A disposble container assembly according to claim 9 wherein:
 said wall includes a circular recess formed therein and said first arm means engages said recess; and
 said second arm means comprises a first finger extending outward from said base, a circular rim pivotally mounted on said first finger and pivotal to a position for surrounding said opening in said container for engaging and retaining said container in said housing, and lock receiving means for locking said circular rim in said engaging position.

11. A secure disposable container assembly for medical sharps and waste, comprising:
a substantially rigid housing having side walls defining an upwardly extending opening surrounded by a peripheral rim;
a semi-rigid inner disposable container for removably positioning in said opening in said housing and having a radial flange for overlapping engagement with said peripheral rim;
latch locking bracket means for permanent attachment to a support structure having first arm means for encircling and receiving said housing for detachable attachment to said support structure;
second arm means movable into clamping position for engaging said peripheral rim for clamping said disposable container in position in said housing; and
locking means for locking said clamping means in position.

12. A secure disposable container assembly according to claim 11 wherein:
said housing is cylindrical in configuration defined by upstanding cylindrical walls terminating in a circular rim defining a circular opening; and
said disposable container is defined by generally frusto conical walls terminating in circular opening and a radial flange surrounding said opening for engaging said circular rim.

13. A secure disposable container assembly according to claim 11 wherein:
said wall includes a circular recess formed therein and said first arm means engages said recess; and
said second arm means comprises a first finger extending outward from said base, a circular rim pivotally mounted on said first finger and pivotal to a position for surrounding said opening in said container for engaging and retaining said container in said housing, and lock means for locking said circular rim in said engaging position.

14. A secure disposable container assembly according to claim 13 wherein:
said bracket means comprises a generally rectangular base plate having means for attachment to a generally vertical support surface;
said first arm means extends outward from base plate and is circular in configuration for encircling said housing; and
said circular rim is disposed above said first arm means.

15. A secure disposable container assembly for medical sharps and waste, comprising:
a substantially rigid cylindrical housing defined by upstanding cylindrical side walls terminating in a circular rim defining an upwardly extending circular opening surrounded by a peripheral rim;
a substantially rigid inner disposable container for removably positioning in said opening in said housing and defined by generally frusto conical walls terminating in circular opening and a radial flange surrounding said opening for overlapping engagement with said circular rim;
latch locking bracket means for permanent attachment to a support structure having first clamping means for encircling and receiving said housing for detachable attachment thereof to said support structure;
second clamping means movable into clamping position for engaging said peripheral rim for clamping said disposable container in position in said housing, said second clamping means comprises hinge means extending outward from said base, a circular rim pivotally mounted on said hinge means and pivotal to a position for surrounding said opening in said disposable container for engaging and retaining said disposable container in said housing; and
locking means for locking said second clamping means in position.

16. A secure disposable container assembly according to claim 15 wherein:
said bracket means comprises a generally rectangular base plate having means for attachment to a generally vertical support surface;
said first clamp means extends outward from base plate and is circular in configuration for encircling said housing; and
said circular rim is disposed above said first clamp means and is pivotal about a horizontal axis.

* * * * *

UNITED STATES PATENT AND TRADEMARK OFFICE
CERTIFICATE OF CORRECTION

PATENT NO. : 4,702,385

DATED : October 27, 1987

INVENTOR(S) : RICHARD A. SHILLINGTON ET AL

It is certified that error appears in the above-identified patent and that said Letters Patent is hereby corrected as shown below:

Claim 9, column 4, line 52, change "8" to --2--.

Claim 11, column 5, line 22, change "clamping" to --second arm--.

Signed and Sealed this

Nineteenth Day of July, 1988

Attest:

DONALD J. QUIGG

Attesting Officer

Commissioner of Patents and Trademarks